(12) United States Patent
Karim et al.

(10) Patent No.: US 9,060,832 B2
(45) Date of Patent: Jun. 23, 2015

(54) FABRICATION OF DENTAL ARTICLES USING DIGITALLY-CONTROLLED REDUCTIVE AND DIGITALLY-CONTROLLED ADDITIVE PROCESSES

(75) Inventors: Naimul Karim, Maplewood, MN (US); Sumita B. Mitra, West Saint Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 420 days.

(21) Appl. No.: 12/741,385

(22) PCT Filed: Nov. 18, 2008

(86) PCT No.: PCT/US2008/083881
§ 371 (c)(1),
(2), (4) Date: May 5, 2010

(87) PCT Pub. No.: WO2009/070469
PCT Pub. Date: Jun. 4, 2009

(65) Prior Publication Data
US 2010/0233655 A1    Sep. 16, 2010

Related U.S. Application Data

(60) Provisional application No. 60/990,674, filed on Nov. 28, 2007.

(51) Int. Cl.
*A61C 13/00* (2006.01)

(52) U.S. Cl.
CPC ......... *A61C 13/0022* (2013.01); *A61C 13/0009* (2013.01); *A61C 13/001* (2013.01); *A61C 13/0013* (2013.01); *A61C 13/0018* (2013.01); *A61C 13/0019* (2013.01)

(58) Field of Classification Search
USPC ............ 700/98, 117, 118, 119, 120; 433/218, 433/219, 222.1, 223
See application file for complete search history.

(56) References Cited

U.S. PATENT DOCUMENTS

| | | | |
|---|---|---|---|
| 4,585,417 A | 4/1986 | Sozio et al. | |
| 5,347,454 A | 9/1994 | Mushabac | |
| 5,944,893 A | 8/1999 | Anderson | |
| 5,972,111 A | 10/1999 | Anderson | |
| 6,190,454 B1 | 2/2001 | Anderson | |
| 2004/0133293 A1 | 7/2004 | Durbin et al. | |
| 2005/0070782 A1 | 3/2005 | Brodkin | |
| 2005/0147944 A1* | 7/2005 | Karim et al. | 433/201.1 |
| 2006/0008777 A1* | 1/2006 | Peterson et al. | 433/223 |
| 2006/0240177 A1 | 10/2006 | Newkirk et al. | |
| 2007/0103460 A1 | 5/2007 | Zhang et al. | |

(Continued)

FOREIGN PATENT DOCUMENTS

| | | |
|---|---|---|
| CN | 1451367 | 10/2003 |
| EP | 1 252 867 A1 | 10/2002 |

(Continued)

*Primary Examiner* — Ryan Jarrett (57) ABSTRACT

By capturing a highly detailed three-dimensional digital model of dentition, a suitable replacement dental article be fabricated with a combination of digitally-controlled reductive processes such as milling and digitally-controlled additive processes such as digital painting. A dental article so-manufactured can provide an aesthetically pleasing, multi-chromatic appearance that closely matches surrounding dentition.

20 Claims, 3 Drawing Sheets

(56) References Cited

U.S. PATENT DOCUMENTS

| | | |
|---|---|---|
| 2007/0182797 A1 | 8/2007 | Free et al. |
| 2007/0188769 A1 | 8/2007 | Rohaly et al. |
| 2008/0015727 A1 | 1/2008 | Dunne et al. |
| 2008/0153067 A1 | 6/2008 | Berckmans et al. |
| 2009/0233258 A1* | 9/2009 | Luthardt et al. .............. 433/223 |

FOREIGN PATENT DOCUMENTS

| WO | WO 2006/031096 A1 | 3/2006 |
|---|---|---|
| WO | WO 2007/051447 A1 | 5/2007 |

* cited by examiner

FABRICATION OF DENTAL ARTICLES USING DIGITALLY-CONTROLLED REDUCTIVE AND DIGITALLY-CONTROLLED ADDITIVE PROCESSES

CROSS-REFERENCE TO RELATED APPLICATIONS

This application is a national stage filing under 35 U.S.C. 371 of PCT/US2008/083881, filed Nov. 18, 2008, which claims priority to U.S. Application No. 60/990,674, filed Nov. 28, 2007, the disclosure of which is incorporated by reference in their entirety herein.

BACKGROUND

1. Field of the Invention

The invention relates to dentistry, and more particularly to fabricating dental articles using a combination of digitally-controlled reductive processes and digitally-controlled additive processes.

2. Description of the Related Art

One technique for fabricating crowns and other dental articles employs a computer-controlled milling machine to shape a mill blank into a desired end product. Most commercially available mill blanks are made of ceramic or some other material suitably hard for use in a final dental restoration, such as porcelain or micaceous ceramics. However, milled dental articles have generally monolithic visual appearance due to the corresponding, monolithic composition of dental mill blanks. It may still require a number of manual finishing steps in order to achieve an appearance consistent with surrounding dentition.

There remains a need for improved automation in the fabrication of highly aesthetic, multi-chromatic dental articles from digital, three-dimensional dental data.

SUMMARY

By capturing a highly detailed three-dimensional digital model of dentition, a suitable replacement dental article can be fabricated with a combination of digitally-controlled reductive processes such as milling and digitally-controlled additive processes such as digital painting. A dental article so-manufactured can provide an aesthetically pleasing, multi-chromatic appearance that closely matches surrounding dentition.

In one aspect, a method disclosed herein includes receiving a digital model of a dental article, the dental article including a volume having a bonding surface shaped to attach to a site in human dentition and a functional surface shaped to replace a dental structure removed from the site; fabricating an understructure for the dental article with a digitally-controlled reductive process, the understructure including a majority of the volume of the dental article; and adding at least one layer to the understructure using a digitally-controlled additive process, thereby providing the dental article.

The dental article may be a restoration selected from the group consisting of a crown, a bridge, an inlay, and an onlay. The dental article may be a denture or an implant. The site may include a prepared surface of a tooth. The functional surface may be created from a three-dimensional scan of the tooth before preparation. The functional surface may be created from a template. The template may be modified using three-dimensional data from dentition surrounding the site. The template may be modified using occlusion data from one or more opposing teeth. The digitally-controlled reductive process may include a milling process. The digitally-controlled additive process may include one or more of stereo-lithography, digital light processing, and three-dimensional printing. Adding at least one layer may include fabricating the at least one layer directly on the understructure. The at least one layer may include a plurality of layers selected to achieve a multi-chromatic appearance of natural dentition. The method may include affixing the dental article to the site. The digital model may include color and opacity information, and adding at least one layer to the understructure may include selecting a material for the at least one layer to correspond to the color and opacity information. The method may include applying a plurality of materials to obtain a multi-chromatic dental article.

In another aspect, a system disclosed herein includes a digitally-controlled milling machine; a digitally-controlled additive device; and a controller coupled to the digitally-controlled milling machine and the digitally-controlled additive device, the controller programmed to receive a digital model of a dental article and to control operation of the digitally-controlled milling machine and the digitally-controlled additive device to fabricate the dental article from a dental mill blank using a combination of additive and reductive processes.

The dental article may include a volume having a bonding surface shaped to attach to a site in human dentition and a functional surface shaped to replace a dental structure removed from the site. The controller may be programmed to fabricate an understructure for the dental article with the digitally-controlled milling machine, the understructure including a majority of the volume of the dental article. The controller may be programmed to add at least one layer to the understructure using the digitally-controlled additive device. The digitally-controlled additive device may include one or more of a stereo-lithography device, a digital light processing device, and a three-dimensional printing device. The dental article may be a restoration selected from the group consisting of a crown, a bridge, an inlay, and an onlay. The dental article may be a denture or an implant.

BRIEF DESCRIPTION OF THE FIGURES

The invention and the following detailed description of certain embodiments thereof may be understood by reference to the following figures.

DETAILED DESCRIPTION

Described herein are systems and methods for fabricating a dental article using a combination of computer-controlled milling and digital painting, based upon a model obtained from a three-dimensional scan of patient dentition. While the description emphasizes certain specific steps and certain types of dental articles, it will be understood that additional variations, adaptations, and combinations of the methods and systems below will be apparent to one of ordinary skill in the art. For example there are a number of variants to computer-controlled milling that may be suitably employed as a digitally-controlled reductive system, and there are a number of variants to digital painting that may be suitably employed as a digitally-controlled additive system. Similarly, various types of cured or partially-cured materials may be employed for various fabrication steps, and a number of three-dimensional scanning technologies are available that might be suitably adapted to obtaining three-dimensional scans for the uses described herein. In addition, while not specifically described below, it will be understood that a coping or other substructure or interim article of dental manufacture may be fabricated using the techniques described herein. All such variations, adaptations, and combinations are intended to fall within the scope of this disclosure.

The following description should be read with reference to the drawings, in which like elements in different drawings are numbered in like fashion. The drawings, which are not necessarily to scale, depict selected illustrative embodiments and are not intended to limit the scope of the disclosure. Although examples of construction, dimensions, and materials are illustrated for the various elements, those skilled in the art will recognize that many of the examples provided have suitable alternatives.

Unless explicitly indicated or otherwise clear from the context, the following conventions are employed in the following disclosure, and are intended to describe the full scope of the inventive concepts herein. All numbers expressing feature sizes, amounts, and physical properties used in the specification and claims are to be understood as being modified by the term "about." Any numerical parameters set forth in this specification and attached claims are approximations that can vary depending upon the desired properties sought to be obtained by those skilled in the art utilizing the teachings disclosed herein. The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise. In a list, the term "or" means one or all of the listed elements or a combination of any two or more of the listed elements.

When a group is present more than once in a formula described herein, each group is "independently" selected, whether specifically stated or not. For example, when more than one M group is present in a formula, each M group is independently selected.

The terms "three-dimensional surface representation", "digital surface representation", "three-dimensional surface map", and the like, as used herein, are intended to refer to any three-dimensional surface map of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

As used herein, the term "room temperature" refers to a temperature of 20° C. to 25° C. or 22° C. to 25° C.

The term "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "dental object", as used herein, is intended to refer broadly to subject matter specific to dentistry. This may include intraoral structures such as dentition, and more typically human dentition, such as individual teeth, quadrants, full arches, pairs of arches which may be separate or in occlusion of various types, soft tissue, and the like, as well as bones and any other supporting or surrounding structures. As used herein, the term "intraoral structures" refers to both natural structures within a mouth as described above and artificial structures such as any of the dental objects described below that might be present in the mouth. As used herein, the term dental article is intended to refer to a man-made dental object. Dental articles may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental articles may also include a "prosthesis" that replaces dentition with removable or permanent structures, such as dentures, partial dentures, implants, retained dentures, and the like. Dental articles may also include "appliances" used to correct, align, or otherwise temporarily or permanently adjust dentition, such as removable orthodontic appliances, surgical stents, bruxism appliances, snore guards, indirect bracket placement appliances, and the like. Dental articles may also include "hardware" affixed to dentition for an extended period, such as implant fixtures, implant abutments, orthodontic brackets, and other orthodontic components. Dental articles may also include "interim components" of dental manufacture such as dental models (full or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects (i.e., dental articles) such as the restorations, prostheses, appliances, hardware, and interim components of dental manufacture as described above. A dental article may be fabricated intraorally, extraorally, or some combination of these.

Terms such as "digital painting", "digital painting process", "computer-controlled painting", "digitally-controlled painting" and the like, as well as verb forms such as "digitally painting", are intended to refer to a computer-controlled painting process, and in particular to such processes that provide for control over a location of paint distribution and a selection among two or more paints for application. A number of technologies may be suitably employed for digital painting provided they can deposit surface layers with sufficient depth, positional accuracy, and material selectively to be usefully employed in coating dental articles. One suitable embodiment may be adapted from Wirejet painting technology formerly available from Pixation Corporation, which applies paint in fluid form. Digitally-controlled wirejet paint heads and systems are described, for example in the following references, each of which is incorporated by reference herein in its entirety: U.S. patent application Ser. No. 08/958,292 to Anderson entitled Metering Device for Paint for Digital Printing filed on Oct. 27, 1997 and issued on Aug. 31, 1999 as U.S. Pat. No. 5,944,893; U.S. patent application Ser. No. 08/878,650 to Anderson entitled Metering Device for Paint for Digital Printing filed on Jun. 19, 1997 and issued on Oct. 26, 1999 as U.S. Pat. No. 5,972,111; U.S. patent application Ser. No. 09/186,220 to Anderson entitled Printer Cartridge filed on Nov. 4, 1998 and issued on Feb. 20, 2001 as U.S. Pat. No. 6,190,454; and U.S. patent application Ser. No. 11/669,387 to Free et al. entitled Printer Having a Print Wire with Alternating Hydrophilic and Hydrophobic Areas to Form Droplets for Printing Inks, filed on Jan. 31, 2007 and published on Aug. 9, 2007 as U.S. Pub. No. 2007/0182797. Any other monochromatic or multichromatic print head suitable for distributing fluids to selected locations of a surface may be similarly employed for digitally-controlled painting. In general, the digital paint head should be capable of delivering paint within a natural dentition color space, either through selective application of different paints or on-the-fly mixing of dyes and other materials. In addition, opacity may be usefully controlled through fillers and other materials within a paint binder.

A "digital wirejet paint head" refers specifically to paint heads of the type used in wirejet printers. More generally, a "digital painting process" may be any of the digital painting techniques described above, or otherwise suitable for use with the systems and methods described herein, including inkjet or laser printing technologies that can be adapted to distribute paints in fluid form. This includes, for example, solid applications, which may be baked to a final coat, or gaseous (e.g., as a gas or as a gaseous suspension) applications such as spray painting. It will be understood that a variety of materials may be applied in fluid form in a digital painting process, including oil-based paints, acrylic paints, urethanes, polyurethanes, enamels, and so forth. A paint as used herein may include pigments for color, binders for structure (e.g., acrylics, polyurethanes, polyesters, melamine resins, epoxy, oil), and solvents or the like for adjusting viscosity (e.g., aliphatics, aromatics, alcohols, ketones, petroleum distillates, esters, glycol ethers, low-molecular weight synthetic resins, etc.), as well as other miscellaneous additives to control handling properties or provide improved performance in applied paint (e.g., antifreeze, antibacterials, pigment stability, etc.). Paints may also be categorized according to curing mechanism, which may, for example, include drying by solvent evaporation, oxidative crosslinking, catalyzed polymerization, and coalescence. In the typical dental applications described herein, any such material that can be applied in fluid form may be used, provided it can be dried, heated, or otherwise cured into a surface suitable for use in a dental article.

Figure 1:
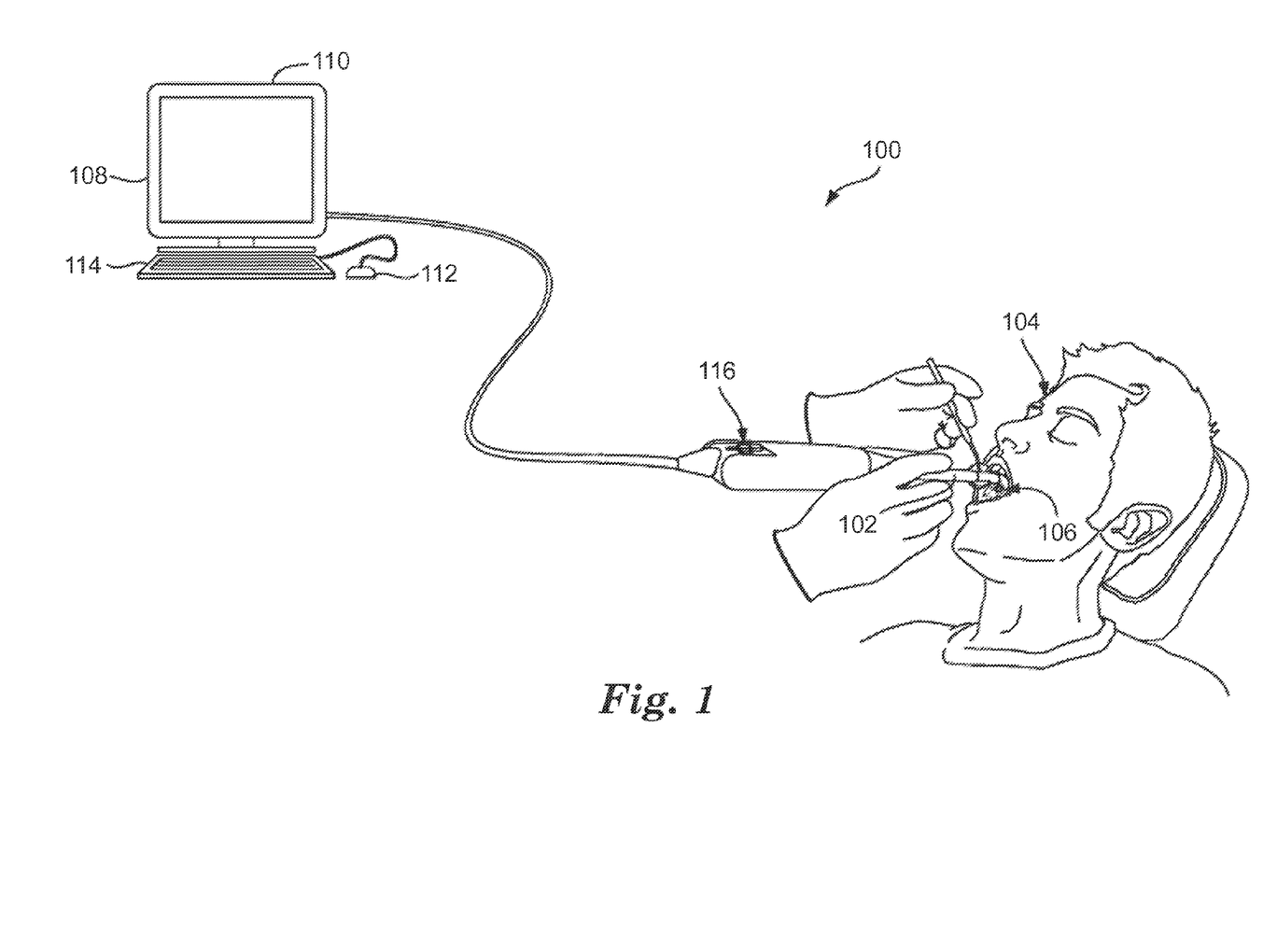
FIG. 1 shows a three-dimensional scanning system.

FIG. 1 shows a three-dimensional scanning system that may be used with the systems and methods described herein. In general, the system 100 may include a scanner 102 that captures images from a surface 106 of a subject 104, such as a dental patient, and forwards the images to a computer 108, which may include a display 110 and one or more user input devices such as a mouse 112 or a keyboard 114. The scanner 102 may also include an input or output device 116 such as a control input (e.g., button, touchpad, thumbwheel, etc.) or a display (e.g., LCD or LED display) to provide status information.

The scanner 102 may include any camera or camera system suitable for capturing images from which a three-dimensional point cloud may be recovered. For example, the scanner 102 may employ a multi-aperture system as disclosed, for example, in U.S. patent application Ser. No. 11/530,420 to Rohály et al. entitled Three-Channel Camera Systems with Collinear Apertures, filed on Sep. 8, 2006 and published on Aug. 16, 2007 as U.S. Pub. No. 2007/0188769, the entire content of which is incorporated herein by reference. While Rohály discloses certain multi-aperture systems, it will be appreciated that any multi-aperture system suitable for reconstructing a three-dimensional point cloud from a number of two-dimensional images may similarly be employed. In one multi-aperture embodiment, the scanner 102 may include a plurality of apertures including a center aperture positioned along a center optical axis of a lens, along with any associated imaging hardware. The scanner 102 may also, or instead, include a stereoscopic, triscopic or other multi-camera or other configuration in which a number of cameras or optical paths are maintained in fixed relation to one another to obtain two-dimensional images of an object from a number of slightly different perspectives. The scanner 102 may include suitable processing for deriving a three-dimensional point cloud from an image set or a number of image sets, or each two-dimensional image set may be transmitted to an external processor such as contained in the computer 108 described below. In other embodiments, the scanner 102 may employ structured light, laser scanning, direct ranging, or any other technology suitable for acquiring three-dimensional data, or two-dimensional data that can be resolved into three-dimensional data.

In one embodiment, the scanner 102 is a handheld, freely positionable probe having at least one user input device 116, such as a button, lever, dial, thumb wheel, switch, or the like, for user control of the image capture system 100 such as starting and stopping scans. In an embodiment, the scanner 102 may be shaped and sized for dental scanning More particularly, the scanner may be shaped and sized for intraoral scanning and data capture, such as by insertion into a mouth of an imaging subject and passing over an intraoral surface 106 at a suitable distance to acquire surface data from teeth, gums, and so forth. The scanner 102 may, through such a continuous acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthetic, to ensure proper fitting using a previous scan of corresponding dentition, such as a tooth surface prepared for the prosthetic.

Although not shown in FIG. 1, it will be appreciated that a number of supplemental lighting systems may be usefully employed during image capture. For example, environmental illumination may be enhanced with one or more spotlights illuminating the subject 104 to speed image acquisition and improve depth of field (or spatial resolution depth). The scanner 102 may also, or instead, include a strobe, flash, or other light source to supplement illumination of the subject 104 during image acquisition.

The subject 104 may be any object, collection of objects, portion of an object, or other subject matter. More particularly with respect to the dental fabrication techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. In other embodiments where, for example, a completed fabrication is being virtually test fit to a surface preparation, the scan may include a dental prosthesis such as an inlay, a crown, or any other dental prosthesis, dental hardware, dental appliance, or the like. The subject 104 may also, or instead, include a dental model, such as a plaster cast, wax-up, impression, or negative impression of a tooth, teeth, soft tissue, or some combination of these.

The computer 108 may be, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. This system may be operated to capture approximately 1,500 points per image set in real time using the techniques described herein, and store an aggregated point cloud of over one million points. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the subject 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110.

Communications between the computer 108 and the scanner 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the scanner 102 to the computer 108 may be secured. The computer 108 may generate control signals to the scanner 102 which, in addition to image acquisition commands, may include conventional camera controls such as focus or zoom.

In an example of general operation of a three-dimensional image capture system 100, the scanner 102 may acquire two-dimensional image sets at a video rate while the scanner 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system employs camera motion estimation to avoid the need for independent tracking of the position of the scanner 102. One useful example of such a technique is described in commonly-owned U.S. patent application Ser. No. 11/270,135 to Zhang et al. entitled Determining Camera Motion, filed on Nov. 9, 2005 and published on May 10, 2007 as U.S. Pub. No. 2007/0103460, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In some embodiments, the display may include a touch screen interface using, for example capacitive, resistive, or surface acoustic wave (also referred to as dispersive signal) touch screen technologies, or any other suitable technology for sensing physical interaction with the display 110.

Figure 2:
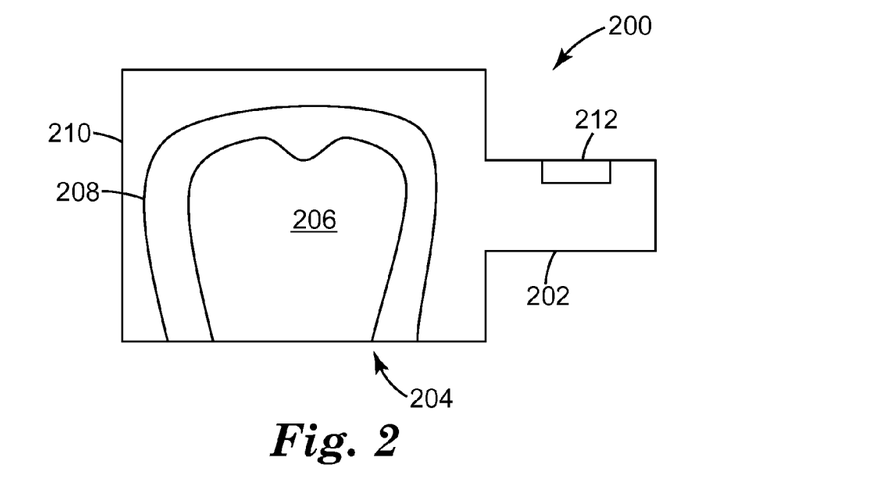
FIG. 2 shows a dental mill blank.

FIG. 2 shows an SMC dental mill blank that may be used with the systems and methods described herein in a side view. In general, a dental mill blank 200 includes a stem 202 and a body 204. The dental mill blank 200 may be a compound mill blank that includes a volume encompassing an internal material 206, an exterior material 208, and an outer layer 210. The dental mill blank 200 may also optionally include an identifier 212 such as a bar code or Radio-Frequency Identification (RFID) tag. It will be understood that while compound SMC mill blanks are described below, and while certain advantages may be realized using compound SMC mill blanks, a mill blank formed from a single SMC material, or an SMC material and some other material, or some other material such as a ceramic may also or instead be suitably employed with the systems and methods described herein.

The stem 202 may optionally be provided to support the blank 200 during milling or other handling, and may be shaped to fit into a corresponding chuck or other support of a milling machine or similar hardware for shaping the blank 200 through the selective removal of material therefrom. In some embodiments, the stem 202 may be cured prior to milling for improved mechanical support of the blank 200.

Where the mill blank 200 is a compound mill blank, the body 204 may have any shape and size suitable for accommodating the internal material 206 and exterior material 208 as described below, and may further include an optional outer layer 210 as described generally below. For a mill blank 200 formed from a single material, the mill blank may more generally have a body 204 of adequate volume to mill a desired dental article therefrom. It will be understood that the blank 200 may be selected or fabricated to match a predetermined tooth size, as determined for example by direct measurement of a site for which a restoration or the like is to be fabricated.

For a compound mill blank 200, the internal material 206 may be any of the SMC materials described above. The internal material 206 may be spatially distributed within the dental mill blank in a manner substantially corresponding to a distribution, in a cured and milled dental article fabricated from the blank 200, of dentin in a natural tooth structure. This distribution may vary according to the size or type of tooth for which a dental article is to be milled. For example, for a restoration the distribution may vary according to whether the restoration is a crown, a bridge, an inlay, an onlay, or a veneer. The internal material 206 may be selected to achieve one or more optical properties similar or identical to dentin in a dental article milled from the blank 200. Thus for example the internal material 206 may be selected to have a translucence, color, or shade similar or identical to that of dentin, or may be selected to provide an appearance in the resulting restoration of the desired optical property or properties. Similarly, the internal material 206 may be selected to achieve one or more mechanical (i.e., structural) properties similar or identical to dentin in a cured dental article milled from the blank 200.

Thus for example the internal material 206 may be selected to support a tooth structure in ordinary use, or more generally to provide a desired degree of resistance to fracture, hardness, pliability or the like to a core region of a restoration. In particular, these characteristics may be selected to match the corresponding mechanical properties of a natural tooth structure in a cured dental article fabricated from the blank 200.

The exterior material 208 may be any of the SMC materials described above. The exterior material 208 may be spatially distributed within the dental mill blank in a manner substantially corresponding to a distribution, in a cured and milled dental article fabricated from the blank 200, of enamel in a natural tooth structure. While the interior surface of this material 208 is defined by a mating exterior surface of the internal material 206, the exterior surface of the exterior material 208 may extend as appropriate to provide a required buffer for milling on all surfaces. The exterior material 208 may optionally extend to the extent of the body 204, thus omitting any separate outer layer 210 from the mill blank. The distribution of the exterior material 208 may vary according to the size or type of tooth for which a dental article is to be milled. For example, for a restoration the distribution may vary according to whether the restoration is a crown, a bridge, an inlay, an onlay, or a veneer. The exterior material 208 may be selected to achieve one or more optical properties similar or identical to enamel in a dental article milled from the blank 200. Thus for example the exterior material 208 may be selected to have a translucence, color, or shade similar or identical to that of enamel, or may be selected to provide an appearance in the resulting restoration of the desired optical property or properties. Similarly, the exterior material 208 may be selected to achieve one or more mechanical (i.e., structural) properties similar or identical to enamel in a cured dental article milled from the blank 200. Thus for example the exterior material 208 may be selected to provide a desired hardness, chip resistance, stain resistance, wear resistance, polish retention, and the like to an external surface of a restoration. In particular, these characteristics may be selected to match the corresponding mechanical properties of a natural tooth structure in a cured dental article fabricated from the blank 200.

The outer layer 210 may optionally be provided to serve any number of auxiliary functions. This may include, for example, shaping the blank 200 for convenient handling, packaging, or shipping, as well as protecting the interior of the blank prior to milling, such as to avoid unwanted deformation during stacking or substantial temperature excursions. The outer layer 210 may be millable, or otherwise removable from the blank 200 prior to milling.

The mill blank 200 may optionally include an identifier 212. The identifier 212 may be a bar code, RFID tag, or other identifier that uniquely identifies the blank 200 or associates the blank 200 with one or more properties. The identifier 212 may, for example, be a bar code, serial number, or other human-readable or machine-readable indicia on an exterior surface of the blank 200. The identifier 212 may also be affixed to packaging for the blank 200. The identifier 212 may also, or instead, include an RFID tag or the like physically embedded within the blank 200. In these latter embodiments, the RFID tag may be positioned in a portion of the blank, such as the outer layer 210, that is intended to be removed by milling, or the RFID tag may be positioned within the internal material 206 so that a restoration or other dental article fabricated from the blank 200 carries the information within the RFID tag. In one embodiment, the identifier 212 may encode a unique identification number for the blank 200. This number may be used to obtain any information cross-referenced to that unique number, which may include data concerning the spatial distribution of SMC materials, the size, shade, and type of SMC materials or dental articles milled therefrom, and any other data useful to a dentist preparing a dental article from the mill blank 200, or useful to a machine such as a computer-controlled milling machine that operates on the mill blank 200. In another aspect, the identifier 212 may directly encode data concerning the blank such as a batch number, a shape, a shelf life, and so forth. More generally, any information useful for handling or using the blank 200 may be encoded directly within the identifier 212, or obtained using a unique identifier encoded within the identifier 212. It will be appreciated that the identifier 212 may also, or instead, encode non-unique information that is in turn used to obtain relevant data for the blank 200. All such variations to and combinations of the foregoing are intended to fall within the scope of this disclosure.

Figure 3:
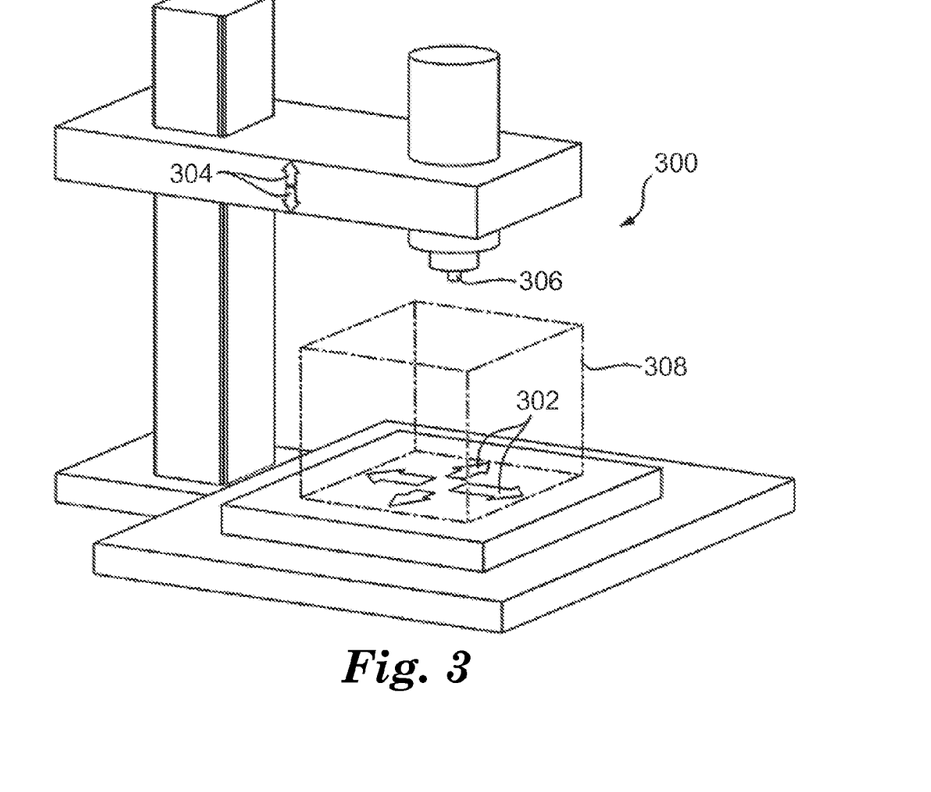
FIG. 3 shows a digitally-controlled reductive system.

FIG. 3 shows a milling machine that may be used with the systems and methods herein. In particular, FIG. 3 illustrates a Computerized Numerically Controlled ("CNC") milling machine 300 including a table 302, an arm 304, and a cutting tool 306 that cooperate to mill under computer control within a working envelope 308. In operation, a workpiece (not shown) may be attached to the table 302. The table 302 may move within a horizontal plane and the arm 304 may move on a vertical axis to collectively provide x-axis, y-axis, and z-axis positioning of the cutting tool 306 relative to a workpiece within the working envelope 308. The cutting tool 306 may thus be maneuvered to cut a computer-specified shape from the workpiece.

Milling is generally a reductive technology in that material is subtracted from a block rather than added. Thus pre-cut workpieces approximating commonly milled shapes may advantageously be employed to reduce the amount of material that must be removed during a milling job, which may reduce material costs and/or save time in a milling process. More specifically in a dental context, it may be advantageous to begin a milling process with a precut piece, such as a generic coping, rather than a square block. A number of sizes and shapes (e.g., molar, incisor, etc.) of preformed workpieces may be provided so that an optimal piece may be selected to begin any milling job. Various milling systems have different degrees of freedom, referred to as axes. Typically, the more axes available (such as 4-axis milling), the more accurate the resulting parts. High-speed milling systems are commercially available, and can provide high throughputs.

In addition a milling system may use a variety of cutting tools, and the milling system may include an automated tool changing capability to cut a single part with a variety of cutting tools. In milling a dental model, accuracy may be adjusted for different parts of the model. For example, the tops of teeth, or occlusal surfaces, may be cut more quickly and roughly with a ball mill and the prepared tooth and dental margin may be milled with a tool resulting in greater detail and accuracy.

All such milling systems as may be adapted for use with the dental mill blanks 200 described herein are intended to fall within the scope of the term "milling" as used herein, and a milling process may employ any such milling systems. More generally, as used herein "milling" may refer to any reductive process including abrading, polishing, controlled vaporization, electronic discharge milling (EDM), cutting by water jet or laser or any other method of cutting, removing, shaping or carving material, unless a different meaning is explicitly provided or otherwise clear from the context. Inputs to the milling system may be provided from three-dimensional scans of dentition using, e.g., the scanner 102 of FIG. 1, three-dimensional scans of working models (which may also be created from a three-dimensional scan), CAD/CAM models (which may also be derived from a three-dimensional scan), or any other suitable source. It should be further understood that, while milling is one example of a digitally-controlled reductive technique, and a computer-controlled milling machine is a readily commercially available digitally-controlled reductive device, that other techniques for removing material under computer control are also known, and may be suitably adapted to use as a digitally-controlled reductive method or system as disclosed herein. This includes, for example, cutting, skiving, sharpening, lathing, abrading, sanding, and the like. Such uses are intended to fall within the scope of this disclosure.

In one aspect, the digitally-controlled reductive device may be fast relative to the additive process so that a majority of the volume of an article can be produced quickly using reductive techniques. In another aspect, the digitally-controlled reductive device may work on high-strength materials (or materials that are curable to high strength) so that the resulting volume of a final product provides strength suitable for its intended application. In another aspect, the digitally-controlled reductive device may provide high spatial resolution to achieve good fit with mating surfaces such as a prepared tooth surface.

Figure 4:
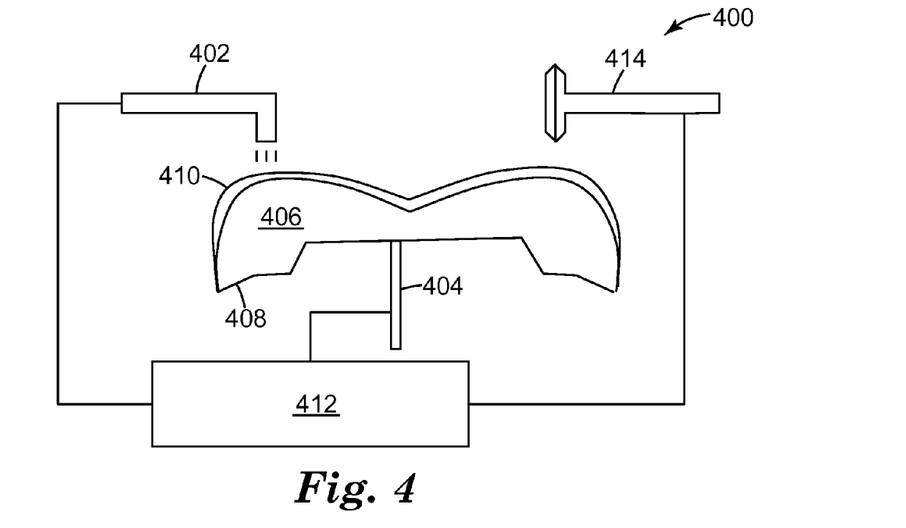
FIG. 4 shows a digitally-controlled additive system.

FIG. 4 shows a device 400 for digitally painting a dental article. In general, the device 400 includes a digital paint head 402, a mounting device 404 holding a dental article 406 that has a bonding surface 408 and a functional surface 410, and a controller 412. The device 400 may also incorporate a milling machine 414 or other cutting tool for reductive processes.

The digital paint head 402 may be any device coupled to a digital painting system for digitally-controlled distribution of paint in a digitally-controlled additive process. The digital painting system may provide for computer control of type of paint, dye mixture, thinning, and so forth, and may also or instead provide computer selection among two or more different paints for application at a particular location. In one aspect, the digital paint head 402 may itself have a controllable position so that the head 402 can be steered over a three-dimensional surface to be painted, or the digital paint head 402 may remain fixed while an object is moved (under computer control) beneath it. The digital paint head 402 may apply paint as droplets, a gaseous suspension, a fluid stream, or in any other manner suitable for controlling distribution on a target. Also as noted above, any substance suitable for use as a coating of dental articles and available in a fluid form may be employed with the digital paint head 402 described herein. In one aspect, the digital paint head may be a digitally-controlled wirejet paint head based upon painting technology formerly sold under the Wirejet brand by Pixation Corporation. Any other print head suitable for distributing fluids to selected locations of a surface may be similarly employed. In general, the digital paint head should be capable of delivering paint within a natural dentition color space, either through selective application of different paints or on-the-fly mixing of dyes and other materials. In addition, opacity may be usefully controlled through fillers and other materials within a paint binder.

It should be understood that, while digital painting is one example of a digitally-controlled additive technique, and a wirejet printer or other digitally-controlled painting system is a digitally-controlled additive device as that term is used herein, that other techniques for adding material under computer control are also known, and may be suitably adapted to use as the digitally-controlled additive methods and systems disclosed herein. This includes, for example, three-dimensional jet printing, stereolithography, digital light processing, and the like. Such uses are intended to fall within the scope of this disclosure. In one aspect, an additive process may provide an aesthetic surface with respect to, e.g., color, opacity, sheen, and the like. In another aspect, the additive process may provide desired surface properties such as texture, polish retention, or wear resistance.

The mounting device 404 may be any device suitable for retaining the dental article 406 in a desired position. This may include clamps, grips, adhesives, mechanical friction fits (which may be machined into the dental article 406), and so forth. In one aspect, the mounting device 404 may retain the dental article 406 in a substantially fixed position. In another aspect, the mounting device 404 may be operable to move the dental article 406 in translation or rotation among any number of axes in order to position a desired point on a surface of the dental article 406 beneath the paint head 402 (or the cutting tool 414). Three translational degrees of freedom and two rotational degrees of freedom may be provided with suitable electromechanical components, and may suffice to operate on any surface of the dental article 406 to be coated with a stationary paint head. In another aspect, motion control may be distributed across the digital paint head 402 and mounting device 404. Thus for example the mounting device 404 may impart a controlled rotational orientation to the dental article 412 around a single axis, while the digital paint head 402 can be translated along two axes (e.g., parallel to the rotational axis, and orthogonal to the rotational axis) so that combined motion of the mounting device 404 and digital paint head 402 can position the paint head 402 to apply paint to any surface region of the dental article 406.

The dental article 406, which may be any of the dental articles described above, may include a bonding surface 408 and a functional surface 410. The bonding surface 408 may be shaped to fit onto a mating prepared tooth surface in a dental patient's dentition. The form of the bonding surface 408 may be determined for example through physical impressioning or scanning of the prepared tooth surface. The functional surface 410 may replace a surface of a natural tooth with corresponding structural and aesthetic properties. The functional surface 410 may be formed of any substance suitable for, or curable into a form suitable for, intraoral use, and may be constructed using the digital painting techniques described herein.

The controller 412 may communicated with the digital paint head 402 (or an associated digital painting system) to control distribution of paint to the dental article 406. This may include selective application of different paints to different locations of the dental article, as well as selective application of different paints to different layers of the functional surface 410, which may be formed from any number of digitally painted layers. The controller 412 may control a position of the digital paint head 402, or may control a position of the mounting device 404 so that different surfaces of the dental article 406 are exposed to the paint head. In positioning the dental article 406, the controller 412 may employ a digital, three-dimensional model of the dental article 406, along with information concerning the color, opacity, texture, and the like of the dental article 406 along the surface thereof. It will be understood that while the digital paint head 402 is intended for coating the functional surface 410 of the dental article 406, the paint head may also, or instead, be usefully employed to apply sealants, adhesives, adhesive precursors, or any other useful materials to the bonding surface 408 or the functional surface 410.

A cutting tool 414 or other milling or cutting device may be usefully included in the device 400 for digitally-controlled reductive operations. The cutting tool 414 may operate under control of the controller to shape one or more surface of the dental article 406, either by moving the cutting tool 414 or by moving the dental article 406 with a movable mount 404, or some combination of these. While a single cutting tool 414 is illustrated, it will be appreciated that many computerized milling machines provide a number of cutting tools and/or a cutting tool with interchangeable cutting instruments having different roughness, hardness, and shape. As with the digital paint head 402, the cutting tool 414, or an associated milling machine, or the controller 412, may use a three-dimensional model of the dental article to control material removal from surfaces of the dental article 406. In an embodiment, the device 400 may be employed to receive a mill blank, shape the mill blank, and finish the shaped article with one or more layers of paint, all under control of the controller 412.

Figure 5:
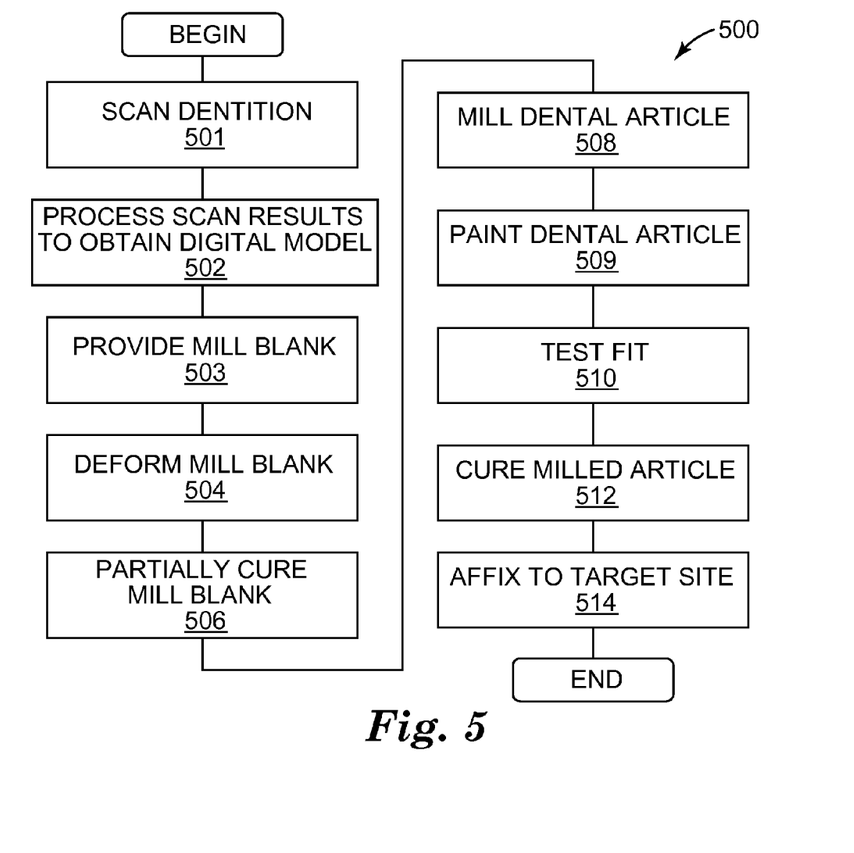
FIG. 5 shows a method for fabricating a dental article.

FIG. 5 shows a method for fabricating a dental article using digitally-controlled reductive and digitally-controlled additive processes.

The process 500 may begin by scanning dentition as shown in step 501. This may include an acquisition of a three-dimensional surface representation or other digital model of a patient's dentition using, e.g., the scanning system described above with reference to FIG. 1. Where a tooth surface is prepared to receive a restoration or the like, step 501 may include a scan before preparation to capture the original, natural shape of the tooth structure being replaced. Step 501 may also, or instead, include a scan of the prepared tooth surface, which may be used in subsequent steps to fabricate a mating, bonding surface of a dental article. Step 501 may also, or instead, include a scan of surrounding dentition including, for example, an opposing arch, neighboring teeth, soft tissue, and the like, any of which might be usefully employed in computer-assisted design of a dental article for the prepared tooth surface.

As shown in step 502, the scan results from step 501 may be processed to obtain a digital model for a computer-controlled milling machine. This may include a wide array of modeling steps. For example, a preliminary or final digital model may be obtained through superposition of pre- and post-preparation scans of a tooth surface, thus permitting the direct fabrication of a replacement article that corresponds physically to the removed structure. A number of dental CAD tools also exist that may be used to create models for restorations and the like from preliminary scan-based models, or from generic tooth models and the like in a dental CAD model library or the like. In addition, some combination of these techniques may be employed.

In one aspect, the model may be adjusted to compensate for shrinkage that occurs during curing of SMC materials. SMC materials may shrink in predictable manners during curing. For example, for light-based curing, monolithic shrinkage in the range of 2% (depending, of course, upon the particular materials) might be expected, provided the light fully penetrates an article that is being cured. Under such conditions, the digital model may be linearly expanded in all dimensions, so that a resulting cured article matches, e.g., an actual prepared tooth surface within a dental patient's dentition. More complex shrinkage algorithms may be required where, for example, articles are partially cured (with respect to degree of curing or location of curing) during handling, or where curing is initiated at a surface of an article. Creating and applying suitable algorithms is within the skill of one of ordinary skill in the relevant arts.

Once a digital model has been obtained, a mill blank may be provided, as shown in step 503. The mill blank may be any of the mill blanks described above including monolithic SMC mill blanks, compound SMC dental mill blanks, other mill blanks incorporating SMC materials, or mill blanks formed from ceramic or similar materials. The mill blank may be selected using any of the criteria described above including, for example, the shape of a desired restoration, the size of a tooth being restored, the type of tooth being restored, and optical characteristics such as color, shade, opacity, and so forth. These criteria may be objectively determined using image analysis including computerized review of image/video data to determine optical and aesthetic properties for a dental article. Image analysis may also or instead include dimensional analysis of three-dimensional data to determine a size, shape, type, or other physical characteristics of the dental article. These criteria may also, or instead, be subjectively determined by a dental professional such as during a patient visit. In one aspect, a suitable mill blank may be selected using a bar code, RFID tag, or other identifier attached to or imprinted on the mill blank.

As shown in step 504, the mill blank may optionally be deformed where the mill blank is fashioned from a deformable, curable material such as any of the SMC materials described above. This may be, for example, a controlled deformation to adapt the mill blank to a specific tooth structure of a dental patient, such as by adapting the mill blank to a particular tooth shape or size. As a significant advantage, this technique may permit a significant reduction in the types of mill blanks required for a range of restorations and other dental procedures. Deformation may be performed, for example, by direct manual deformation of the blank by a dental professional or technician, or using a tool or machine adapted to apply incremental changes along a dimension such as the height or width of the mill blank.

As shown in step 506, the blank may optionally be partially cured. This may include, for example, curing to preserve the deformation applied in step 504 during milling, or more generally curing the blank to prepare for milling. This may also include partial spatial curing, such as curing the stem or other support structures for the mill blank. It will be appreciated that such interim curing steps are optional, and will depend on the particular milling procedure and SMC materials being used, as well as the dental article being fabricated.

As shown in step 508, the mill blank may then be milled into a dental article using any of the milling techniques described above. As generally noted above, the milled dental article may be a restoration such as a crown, a bridge, an inlay, an onlay, a veneer, and the like, as well as any other dental article that replaces natural dentition. For example, the techniques described herein may be suitably adapted to the manufacture of a prosthesis such as a denture or implant. As noted above, while milling is one reductive process that may be usefully employed with the systems and methods described herein, other reductive processes are known, and are intended to fall within the scope of this disclosure.

As shown in step 509, the mill blank may be digitally painted using, for example, the digital painting system described above with reference to FIG. 4. More generally, other additive processes are known, and any such process that can be adapted to use with the systems and methods described herein is intended to fall within the scope of this disclosure.

Step 509 may include a variety of preparation steps. The milled article from step 508 may be dried or cleaned such as to remove milling lubricants or other contaminants. The article may trimmed from any supporting structures, and sanded or otherwise smoothed. Where curable materials are employed in the milled article, the article may be partially or fully cured. In addition, a sealant or primer may be applied to the article prior to the application of aesthetic or functional paint layers.

In general, a variety of fluids may be usefully employed to digitally paint a dental article. This may include porcelain, resins, acrylic polymers, and any other suitable material. Using a digitally controlled painting process, an outer layer for the understructure may be applied with different colors in different areas. In addition, multiple layers may be applied with varying colors and opacities to build a surface closely resembling natural dentition. In one aspect, visual information concerning color may be captured from a dental patient's natural dentition, and this color information may be applied to create a corresponding surface on the dental article. Various dyes may be used to obtain different colors, which dyes may be provided to a digital painter as a number of discrete paint source selections, or may be added as paint is distributed from a paint head to permit computer-controlled color generation. In other embodiments, paints having different discrete colors may be applied by two or more paint heads or print heads concurrently to obtain a mixed color. The digital painting system may provide a movable paint head, or the dental article may be secured to a movable mount that provides translation and rotation along a number of axes so that areas on the surface of the dental article can be selectively positioned in front of a fixed paint head, or some combination of these. However controlled, a digital model of the dental article or the milled understructure for the dental article may be employed to control positioning. The digital painting system may also, or instead, include position or range detection to help ensure accurate distribution of paint on a target article.

After digitally painting the article, the paint may be cured, and any additional layers may be added including sealants, adhesives, or additional layers to provide a more natural look or feel to the article. Paints may be cured through evaporation of solvents, thinners and the like, or may require heat, light, pressure, vacuum, electromagnetic waves or the like to initiate or quicken polymerization or other curing processes depending, of course, on the nature of the materials used in the outer layer. Curing may be achieved or accelerated by two or more cycles of curing conditions.

After completion of digitally-controlled additive steps as described above, the process may proceed to step 510 where the milled and painted (or otherwise fabricated through a combination of reductive and additive technologies) dental article may be test fit to a site in a patient's dentition. This may be performed directly on a patient's dentition, or using a dental model, an articulator, or the like. So for example, the dental article may be placed into an articulating model, and manual adjustments may be made to static or dynamic occlusal fit. Any number of test fits may be performed, after which manual adjustments or re-milling may be performed to adjust occlusal fit, proximal contacts, and the like or otherwise reshape the dental article to obtain a desired exterior shape.

As shown in step 512, once an adequate fit has been achieved the article may optionally be cured to final hardness where additional curing is required for the milling material or any layers added to the surface thereof. Additional reshaping and fitting may be performed after curing to final hardness.

As shown in step 514, the final dental article may be permanently affixed to a target site in a patient's dentition such as by adhering the article using any number of suitable dental adhesives. Additional reshaping and fitting may be performed after affixing to the target site, for example in response to patient observations concerning fit.

It will be understood that the above process 500 is merely exemplary. Any number of adaptations may be made, and steps may be added or removed from the process 500 as described. For example, where SMC materials are employed, the entire dental article may be retained in an at least partially uncured state until the article is permanently affixed to a target site. This technique usefully permits a degree of deformation of the dental article to more closely mate with a prepared tooth surface or surrounding dentition. In another aspect also suitable for use with SMC materials, the entire article except for the portion mating to a prepared tooth surface may be fully cured, with malleability preserved at the mating surface to achieve a closer final fit. All such variations as would be clear to one of ordinary skill in the art are intended to fall within the scope of this disclosure.

It will be appreciated that various aspects of the methods described above including operation of the controller 412, digitally-controlled reductive system 300, and other components may be realized in hardware, software, or any combination of these suitable for the data acquisition and fabrication technologies described herein. This includes realization in one or more microprocessors, microcontrollers, embedded microcontrollers, programmable digital signal processors or other programmable devices, along with internal and/or external memory. The realization may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as the scanning device, milling machine, and so forth in a number of ways or all of the functionality may be integrated into a dedicated, standalone device. All such permutations and combinations are intended to fall within the scope of the present disclosure.

While the invention has been disclosed in connection with certain preferred embodiments, other embodiments will be recognized by those of ordinary skill in the art, and all such variations, modifications, and substitutions are intended to fall within the scope of this disclosure. Thus, the invention is to be understood with reference to the following claims, which are to be interpreted in the broadest sense allowable by law.

What is claimed is:

1. A method comprising:
receiving a digital model of a dental article for a dental patient, the dental article including a volume having a bonding surface shaped to attach to a site in human dentition and a functional surface shaped to replace a dental structure removed from the site;
fashioning a mill blank to fabricate the dental article from a first material, the first material being a deformable, curable material;
curing the mill blank;
receiving visual information including color from natural dentition of the dental patient;
fabricating an understructure for the dental article from the mill blank with a digitally-controlled reductive process, the understructure forming the structure of the dental article including a majority of the volume of the dental article; and adding at least one aesthetic layer of an enamel paint to the understructure using a digitally-controlled paint head and a mounting device collectively operable to move the dental article with three translational degrees of freedom and two rotational degrees of freedom relative to the digitally-controlled paint head, and capable of delivering a controllable color within a natural dentition color space by selecting among two or more different paints for application at a particular location and wherein the digitally-controlled paint head is controlled according to the visual information to create a corresponding surface on the understructure, thereby providing the dental article.

2. The method of claim 1 wherein the dental article is a restoration.

3. The method of claim 2 wherein the restoration includes a crown.

4. The method of claim 3 wherein the restoration includes one or more of a bridge, an inlay, and an onlay.

5. The method of claim 1 wherein the dental article is a denture or an implant.

6. The method of claim 1 wherein the site includes a prepared surface of a tooth.

7. The method of claim 6 wherein the functional surface is created from a three-dimensional scan of the tooth before preparation.

8. The method of claim 6 wherein the functional surface is created from a template.

9. The method of claim 8 wherein the template is modified using three-dimensional data from dentition surrounding the site.

10. The method of claim 9 wherein the template is modified using occlusion data from one or more opposing teeth.

11. The method of claim 1 wherein the digitally-controlled reductive process includes a milling process.

12. The method of claim 1 wherein the digitally-controlled paint head includes a digitally-controlled wirejet paint head configured to deliver paint within a natural dentition color space using on-the-fly mixing of dyes, and further configured to control opacity through fillers within a paint binder.

13. The method of claim 12 wherein adding at least one layer includes fabricating the at least one layer directly on the understructure.

14. The method of claim 1 wherein the at least one layer includes a plurality of layers selected to achieve a multi-chromatic appearance of natural dentition.

15. The method of claim 1 further comprising affixing the dental article to the site.

16. The method of claim 1 wherein the digital model includes color and opacity information, and wherein adding at least one layer to the understructure includes selecting a material for the at least one layer to correspond to the color and opacity information.

17. The method of claim 16 further comprising applying a plurality of materials to obtain a multi-chromatic dental article.

18. A system comprising:
a digitally-controlled milling machine;
a digitally-controlled paint head capable of delivering an enamel paint with a controllable color within a natural dentition color space by selecting among two or more different paints for application at a particular location;
a controller coupled to the digitally-controlled milling machine and the digitally-controlled paint head, the controller programmed to receive a digital model of a dental article for a dental patient and to control operation of the digitally-controlled milling machine to fabricate a shape of the dental article from a mill blank and further to control the digitally-controlled paint head to apply material to a surface of the dental article according to visual information including color from natural dentition of the dental patient;
a mounting device operable in combination with the digitally-controlled paint head to move the dental article in three translational degrees of freedom and two rotational degrees of freedom relative to the digitally-controlled paint head; and
a tool adapted to deform and cure the mill blank prior to machining according to the digital model.

19. The system of claim 18 wherein the digitally-controlled paint head is configured to apply a plurality of layers selected to achieve a multi-chromatic appearance of natural dentition in the dental article.

20. The system of claim 18 wherein digitally-controlled paint head is configured to apply at least one layer including a material selected to correspond to opacity information in the visual information.

* * * * *